United States Patent
Agthoven et al.

(10) Patent No.: US 6,534,279 B1
(45) Date of Patent: Mar. 18, 2003

(54) REAGENT AND METHOD FOR THE PERMEABILIZATION AND IDENTIFICATION OF ERYTHROCYTES

(75) Inventors: André Van Agthoven, Marseille (FR); Christine Fornelli, Marseille (FR)

(73) Assignee: Immunotech, Marseille Cedex (FR)

( * ) Notice: Subject to any disclaimer, the term of this patent is extended or adjusted under 35 U.S.C. 154(b) by 0 days.

(21) Appl. No.: 09/338,505

(22) Filed: Jun. 23, 1999

(30) Foreign Application Priority Data

Jul. 9, 1998 (FR) .......................................... 98 09006

(51) Int. Cl.$^7$ .......................................... G01N 33/553
(52) U.S. Cl. ..................... 435/7.21; 435/810; 435/975; 435/540.5; 514/557; 514/693; 514/694; 514/696; 514/724; 436/520; 436/521; 436/522
(58) Field of Search ................... 514/557, 693, 514/694, 696, 724; 435/2, 810, 975, 540.5, 7.21; 436/520, 521, 522

(56) References Cited

U.S. PATENT DOCUMENTS

| | | | | |
|---|---|---|---|---|
| 4,751,179 A | * | 6/1988 | Ledis et al. ................... 424/3 |
| 5,102,788 A | * | 4/1992 | Cole |
| 5,116,724 A | * | 5/1992 | Delaage et al. ................. 435/2 |
| 5,246,829 A | * | 9/1993 | Delaage et al. ................. 435/2 |
| 5,352,613 A | * | 10/1994 | Tafas et al. .................... 436/63 |
| 5,362,628 A | * | 11/1994 | Haugland et al. ............. 435/18 |
| 5,413,732 A | * | 5/1995 | Buhl et al. ..................... 435/26 |
| 5,432,054 A | * | 7/1995 | Saunders et al. ............... 435/2 |
| 5,457,024 A | * | 10/1995 | Goldbard ....................... 435/2 |
| 5,478,747 A | * | 12/1995 | Hartz, Jr. |
| 5,563,033 A | * | 10/1996 | Lawrence et al. |
| 5,576,424 A | * | 11/1996 | Mao et al. ................... 536/17.9 |
| 5,596,090 A | * | 1/1997 | Hoke et al. |
| 5,599,682 A | * | 2/1997 | Van Agthoven ........... 435/7.24 |
| 5,624,597 A | * | 4/1997 | Buhl et al. ............. 252/182.11 |
| 5,627,213 A | * | 5/1997 | Van Agthoven ............ 514/557 |
| 5,641,628 A | * | 6/1997 | Bianchi ......................... 435/6 |
| 5,679,354 A | * | 10/1997 | Morein et al. |
| 5,686,261 A | * | 11/1997 | Zhang et al. |
| 5,691,160 A | * | 11/1997 | Janmey et al. |
| 5,731,156 A | * | 3/1998 | Golbus .......................... 435/4 |
| 5,750,339 A | * | 5/1998 | Smith ............................ 435/6 |
| 5,853,986 A | * | 12/1998 | Petrie, III et al. ............. 435/6 |
| 5,858,667 A | * | 1/1999 | Dertinger et al. .............. 435/6 |
| 5,861,253 A | * | 1/1999 | Asgari et al. .................. 435/6 |
| 5,906,724 A | * | 5/1999 | Sammons et al. .......... 204/627 |
| 5,948,278 A | * | 9/1999 | Sammons et al. .......... 210/806 |
| 5,962,234 A | * | 10/1999 | Golbus ........................ 435/7.1 |
| 5,977,153 A | * | 11/1999 | Camiener |
| 6,008,052 A | * | 12/1999 | Davis et al. |

FOREIGN PATENT DOCUMENTS

EP     0 469 766     2/1992

* cited by examiner

Primary Examiner—Christopher L. Chin
Assistant Examiner—Pensee T. Do
(74) Attorney, Agent, or Firm—Browdy and Neimark PLLC

(57) ABSTRACT

A process for permeabilizing erythrocytes in which the erythrocytes are subjected successively to the action of (a) a fixing agent containing an aliphatic aldehyde and oligosaccharide, (b) a permeabilizing agent containing a detergent and an oligosaccharide, kit for permeabilizing erythrocytes, kit for immuno-marking fetal erythrocytes, and a process for identifying fetal erythrocytes by immuno-marking.

9 Claims, 2 Drawing Sheets

REAGENT AND METHOD FOR THE PERMEABILIZATION AND IDENTIFICATION OF ERYTHROCYTES

FIELD OF THE INVENTION

The present invention relates to new reagents and a new permeabilization process for erythrocytes as well as its use in the identification of foetal erythrocytes by a new immuno-marking method.

Methods for the cytometric analysis of foetal erythrocytes after marking with fluorescent antibodies inside the erythrocytes already exist.

BACKGROUND OF THE INVENTION

An antibody and its method is sold by the company BIOATLANTIQUE in Nantes (France) under the names "Anticorps monoclonal anti-hemoglobine foetale" and "Protocole pour la cytométrie de flux". This method has the drawback of being lengthy and complicated with twelve washes and 16 hours of incubation.

Another antibody and method is sold by CALTAG LABORATOIRES in Burlingame, Calif. (USA) under the names "Monoclonal antibodies to human foetal hemoglobin" and "Anti-HbF-flow cytometric protocol". This method is shorter with six washes, but uses glutaric aldehyde as a fixing agent, which is not stable at ambient temperature.

It would thus be desirable to have reagents for erythrocytic permeabilization which were stable and capable of being stored for more than a year, and a process for erythrocytic permeabilization which did not contain more than four washing stages and a short incubation, for example thirty minutes.

Now, after lengthy research, the Applicant has discovered that a permeabilization of erythrocytes, without substantial loss of haemoglobin from the cell, can be obtained by treating erythrocytes using a fixing agent and a permeabilizing agent.

SUMMARY OF THE INVENTION

For this reason, a subject of the present invention is a process for the permeabilization of erythrocytes, characterized in that the erythrocytes are subjected successively to the action of
 (a) a fixing agent containing an aliphatic aldehyde and an oligosaccharide,
 (b) a permeabilizing agent containing a detergent and an oligosaccharide.

This new process allows an antibody to enter the erythrocyte and an intracellular antigen to be analyzed. The antigens present in the erythrocyte and particularly those which are carried by the haemoglobin are used for distinguishing and identifying foetal erythrocytes.

The fixing agent contains an aliphatic aldehyde, an oligosaccharide and preferably a sulphated polysaccharide. It is notably in an approximately isotonic or hypertonic and preferably slightly acidic medium.

The aliphatic aldehyde, preferably one containing C1–C5, can be for example paraformaldehyde and particularly formaldehyde.

The aliphatic aldehyde can be present in a concentration of 0.3M to 12.3M, in particular 1.5M to 10M and very particularly 3M to 8.3M. Under preferential conditions of use of the above fixing agent, 6.7M of formaldehyde are used.

The fixing agent also contains an oligosaccharide, preferably a disaccharide. As disaccharides, there can be mentioned for example saccharose, cellobiose, maltose, lactose, gentiobiose, melibiose and in particular trehalose.

The oligosaccharide can be present in a concentration of 0.025M to 1.32M, in particular 0.132M to 1.19M and most particularly 0.26M to 1.06M. Under preferential conditions, the fixing agent contains approximately 0.8M of trehalose.

A sulphated polysaccharide is advantageously used to avoid aggregations including nucleic acids which allows the background noise to be reduced when the above process is used in a process for detecting erythrocytes.

It is found in the fixing agent in a concentration between 0.1 mg/ml and 10 mg/ml. The fixing agent preferably contains approximately 1 mg/ml of dextran sulphate with a molecular weight in the region of 500,000.

The pH of the fixing agent is for example a pH between 3 and 8, in particular between 4 and 7. It is preferably slightly acidic, most particularly between 5 and 6. Under particular conditions, the fixing agent has a pH of approximately 5.5, preferably buffered by a 10 mM solution of sodium dihydrogen phosphate.

The isotonicity of the fixing agent is preferably obtained by the presence of a concentration of 0.15M NaCl.

The permeabilizing agent contains a zwitter-ionic detergent and in particular an anionic detergent. This anionic detergent is for example sodium dioxycholate or N-lauryl sarcoside, and in particular sodium dodecyl sulphate.

The concentration of detergent can be between 0.001% and 10%, and particularly between 0.01 and 5%. Under preferential conditions, the permeabilizing agent contains approximately 0.03% of sodium dodecyl sulphate.

In addition, the permeabilizing agent contains an oligosaccharide, particularly trehalose as described in the case of the fixing agent.

The concentration of trehalose in the permeabilizing buffer is situated for example between 0.0026M and 0.26M, preferably between 0.026M and 0.13M, and most particularly approximately 0.053M.

The pH of the permeabilizing agent is preferably slightly acidic with a pH between 3 and 8, in particular between 5 and 6. The permeabilizing agent has a pH of approximately 5.5 under particular conditions.

The pH of the permeabilizing agent is preferably buffered, advantageously by using 10 mM of sodium dihydrogen phosphate and 10 mM of sodium citrate.

The permeabilizing buffer is preferably approximately isotonic, for example by using a concentration of 0.15M of sodium chloride.

The process according to the invention can be used in particular in the identification of foetal erythrocytes by a new method of immuno-marking using antibodies. For this reason, after fixing and permeabilizing, the erythrocytes are advantageously washed mainly in order to eliminate the detergent which could have a harmful influence on the antibodies used for the revelation of antigens inside the erythrocyte.

The washing agent is preferably a solution having a pH between 3 and 8, and advantageously slightly acidic, between pH 5 and 6. This solution can contain a neutral detergent and can contain a strong acid and base salt such as NaCl and KCl. Preferably, the washing agent does not contain detergent and is hypotonic. Under particularly preferred conditions, the washing agent is distilled or demineralized water.

A subject of the present Application is also a new process for revealing foetal erythrocytes amongst a population of erythrocytes in adult blood.

The best-known method is that of Kleihauer, based on a better resistance of foetal erythrocytes to a hypotonic lysis. Under certain hypotonic conditions, a leaking-out of the haemoglobin of adult erythrocytes is observed, but not foetal erythrocytes, which allows foetal erythrocytes to be distinguished by colour under microscope inspection.

The drawback of this method is that in order to detect a small number of foetal erythrocytes, a large number of erythrocytes must be passed under the microscope, which represents a significant amount of handling. Also, certain pathologies can lead to a modification of the erythrocytes, resulting in a number of false positives. In addition, according to certain reports, this test would not be easy to reproduce.

Other methods are based on the permeabilization of erythrocytes and immuno-marking of foetal haemoglobin (g-haemoglobin) inside foetal erythrocytes with a fluorescent antibody. The latter method allows counting by cytometry but it has the drawback that certain erythrocytes of adult origin can contain foetal haemoglobin (F cells). Equally, in certain diseases such as thalassaemia, the number of adult erythrocytes containing foetal haemoglobin is increased.

Thus, it would be desirable to have a process for immuno-marking foetal erythrocytes which is highly sensitive with reduced possibilities for error.

Thus, a subject of the invention is also the above permeabilization process, characterized in that in addition, (d) the erythrocytes are reacted with two antibodies against two foetal antigens which are expressed on the erythrocyte independently. One, the foetal haemoglobin, is found inside the cell, the other, the i antigen, is found outside the cell.

In the course of this immuno-marking step, the erythrocytes, preferably suspended in water, are advantageously mixed with an equal volume of phosphate buffer containing 5 mg/ml of bovine serum albumin and the two antibodies. During this step, the pH becomes neutral, allowing the antibody to function well and the erythrocyte environment remains slightly hypotonic, allowing a good penetration of antibodies.

The simultaneous immuno-marking of foetal haemoglobin and i with the antibodies marked with two different fluorescent markers allows foetal erythrocytes to be counted as distinct from the "F cells".

The marking of the antibodies with the fluorescent markers such as the fluorescein N-isothiocyanate or phycoerythrin for example can be carried out conventionally as described for example by G. T. HERMANSON in Bioconjugate Techniques, chapter 8.1.1, Fluorescein Derivatives, pages 302–305, Academic Press 1996 or chapter 8.1.7., Phycobiliprotein Derivatives, pages 362–364. The desired antibody can in particular be conjugated with phycoerythrin activated with succinimidyl-4-(N-maleimidomethyl) cyclohexane-1-carboxylate after reduction with 1 mM of DL-dithiothreitol in PBS.

Under preferential implementation conditions for the process described above, monoclonal antibodies of type IgG1 NaM16-2F4 deposited at the Collection Nationale de Microorganismes (CNCM) in Paris on Jun. 23, 1998 under No. 1-2044 are used for marking foetal haemoglobin, and the monoclonal antibody of type IgM NaM61-1A2 deposited at the Collection Nationale de Microorganismes (CNCM) in Paris on Jun. 23, 1998 under No. I-2043 is used for labelling the i antigen.

Under other preferential implementation conditions for the invention, the sensitivity of the test can be increased by adding a marker for the nucleic acids in a third colour.

In three-colour cytometry, the events corresponding to a false "background noise", often leucocytes or dead cells which are rich in DNA, can thus be eliminated.

Under particularly preferred conditions, the marker used for the nucleic acids is a nucleated cell colorant, for example by fixing on the DNA, particularly LDS 751 (MOLECULAR PROBES Inc. Or, USA).

A further subject of the present Application is an erythrocyte permeabilization kit, characterized in that it includes (a) an approximately isotonic fixing agent containing an aliphatic aldehyde and an oligosaccharide, b) a permeabilizing agent containing a detergent and an oligosaccharide.

A further subject of the present Application is a foetal erythrocyte immunomarking kit, characterized in that it contains the above erythrocyte permeabilizing kit as well as two antibodies against two foetal antigens which are expressed independently on the erythrocyte.

Finally, a subject of the present application is a process for identifying foetal erythrocytes by immuno-marking, characterized in that the erythrocytes are successively subjected to the action of:

(a) a fixing agent containing an aliphatic aldehyde and an oligosaccharide in an approximately isotonic or hypertonic medium, (b) a permeabilizing agent containing a detergent or an oligosaccharide operated according to claim 8

(c) a washing agent mainly in order to eliminate the detergent (d) two antibodies against two foetal antigens which are expressed independently on the erythrocyte then the of foetal erythrocytes are detected.

This detection can be carried out by all the well-known methods in the prior art for detecting fluorescent compounds, combined with the use of measurement thresholds or measurement scales.

The preferential conditions for implementing the processes described above apply equally to other objects of the invention described above, in particular the kits.

The following examples illustrate the present Application.

Example 1

Fixing reagent 6.67M formaldehyde
0.8M D (+) trehalose
0.15M sodium chloride
0.01 M sodium dihydrogen phosphate
1 mg/ml dextran sulphate (PM 500.000)
pH 5.5

Permeabilizing reagent 0.001M sodium dodecyl sulphate
0.15M NaCl
0.01M sodium dihydrogen phosphate
0.01M sodium citrate
0.053M D(+) trehalose
pH 5.5

Example 2

Permeabilization procedure

Four samples of blood were selected to be subjected to a permeabilization procedure.

The samples were used with ethylene diamine tetraacetic acid (EDTA) as an anticoagulant.

1. Blood of a male subject.
2. One millilitre of the same blood described in 1 to which 0.01 ml of blood from the umbilical cord taken during the birth of a baby is added.
3. Blood of a pregnant woman whose blood has been examined by the Kleihauer method and for which the result obtained was negative.
4. Blood of a pregnant woman whose blood has been examined by the Kleihauer method and for which the result obtained was positive, giving a value of 0.1% of foetal erythrocytes.

Each sample of 0.01 ml of blood was mixed with 0.1 ml of fixing reagent (Example 1) and the mixture was incubated for 30 minutes at ambient temperature (20–25° C.). After incubation, 3 ml of phosphate buffer (PBS=Phosphate Buffered Saline) was added as a washing agent and the whole was centrifuged at 300 g.

After aspiration, the cells were taken up in 3 ml of permeabilizing reagent (Example 1) and centrifuged at 300 g.

After aspiration, the cells were taken up in 1 ml of demineralized water.

Example 3

Immuno-marking of foetal erythrocytes

20 µl of each of the preparations of Example 2 of erythrocytes suspended in water were mixed with 20 µl of the following preparation:

PBS containing:
50 µg/ml of monoclonal antibodies NaM16-2F4 directed against foetal haemoglobin and conjugated with fluorescein isothiocyanate as described by G. T. HERMANSON in Bioconjugate Techniques, chapter 8.1.1, Fluorescein Derivatives, pages 302–305, Academic Press 1996;
3.12 µg/ml of monoclonal antibodies NaM61-1A2 directed against antigen i and conjugated with phycoerythrin as described by G. T. HERMANSON in Bioconjugate Techniques, chapter 8.1.7., Phycobiliprotein Derivatives, pages 362–364;
3.12 µg/ml of LDS 751 (Molecular Probes, OR, USA).
5 mg/ml of bovine serum albumin (BSA).

After incubation for 15 minutes, 3 ml of phosphate buffer containing 0.17M of formaldehyde was added to each mixture as a washing agent and centrifuged at 300 g for 5 minutes. After aspiration, the cells were taken up in 0.5 ml of phosphate buffer with 0.17M formaldehyde.

The hybridoma corresponding to the monoclonal antibody NaM16-2F4 was deposited at the Collection Nationale de Microorganismes (CNCM) in Paris on Jun. 23, 1998 under No. I-2044. The monoclonal antibody NaM16-2F4 is of IgG1 type. The hybridoma corresponding to the monoclonal antibody NaM61-1A2 was deposited at the Collection Nationale de Microorganismes (CNCM) in Paris on Jun. 23, 1998 under No. I-2043. The monoclonal antibody NaM61 is of IgM type.

Example 4

Cytometric analysis

A Coulter XL cytometer (Miami, Fla., USA) was used for analysing the results. The fluorescent adjustments FL1 and FL2 and the compensations were obtained according to the manufacturer's instructions using a reference sample "Cytotrol" (Coulter No. Cat 6604248), mixed with 20 µl of sample No. 1 of Example 2, and marked with a mixture of CD4-FITC(fluorescein N-isothiocyanate) and CD8-PE (phycoerythrin) (Immunotech, Cat No. IMO747).

The adjustment and compensation of FL4 was obtained with sample 2 of Example 2 after immuno-marking according to Example 3.

DETAILED DESCRIPTION OF THE INVENTION

Figure 1:
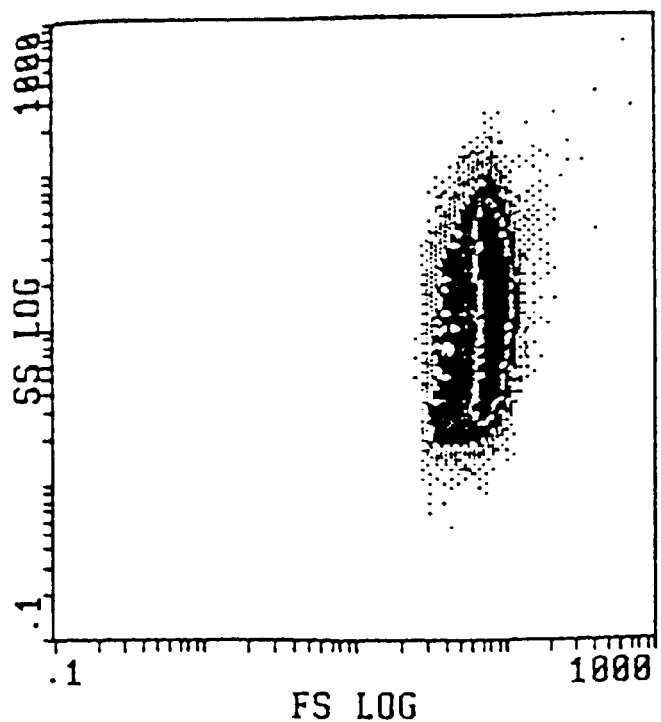
FIG. 1 shows a scattergram of the events of Sample 2 (Example 2) after immuno-marking (Example 3). The events smaller than that of the erythrocytes were excluded by a threshold.

In FIG. 1, a population of homogeneous events of adult and foetal erythrocytes can be observed. A threshold in the forward scatter excludes events of a smaller size than the selected threshold such as those which correspond to platelets and debris. A small number of leucocytes and debris of large size are included in the population.

Figure 2:
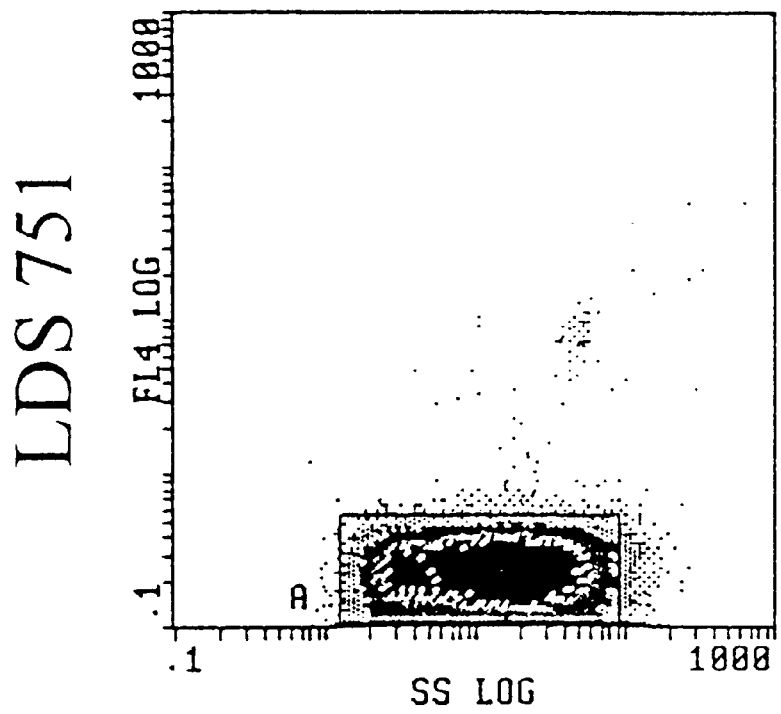
FIG. 2 shows a side scatter analysis and FL4 events of Sample 2 (Example 2) after immuno-marking (Example 3) and the exclusion of events of smaller size as shown in FIG. 1. The LDS 751 positive events (leucocytes and unidentified particles) were excluded from the gate.

In FIG. 2, the same population can be seen as in FIG. 1 represented in side scatter and in FL4, a fluorescent region emitted by LDS751. The LDS751 positive events, and even the leucocytes and debris of large size, are excluded from the analysis by a gate created around the negative events and including the adult and foetal erythrocytes.

Figure 3:
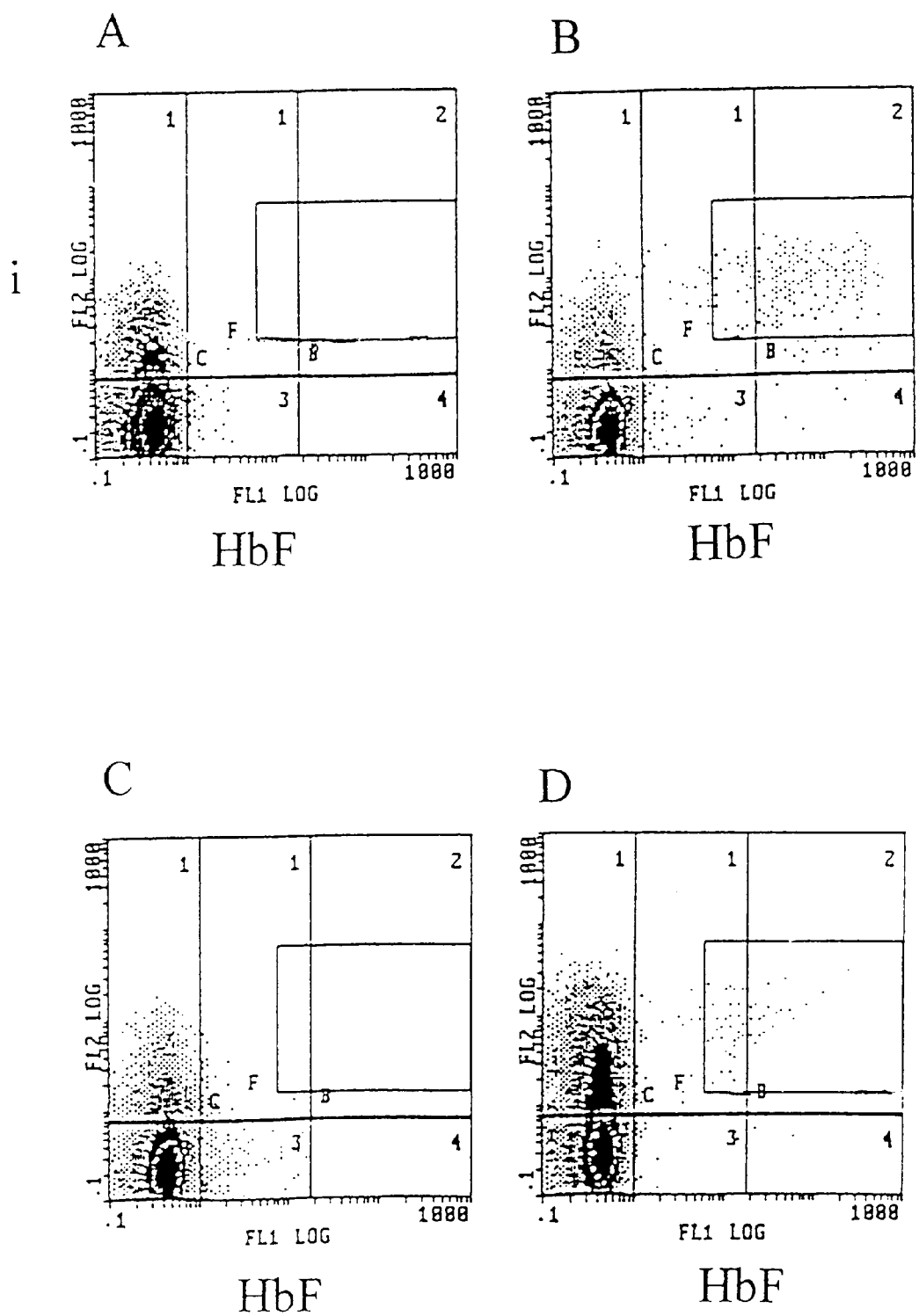
FIG. 3 shows FL1 and FL2 analysis of the erythrocyte populations after immuno-marking (Example 3) and included in the gate as shown in FIG. 2.

In FIG. 3, where Samples 1, 2, 3, 4 (Sample 1 (Example 2): erythrocytes from adult blood serving as a control; Sample 2 (Example 2): erythrocytes from adult blood mixed with 0.01 v/v of cord blood; Sample 3 (Example 2): erythrocytes from Kleihauer negative blood serving as a control; Sample 4 (Example 2): erythrocytes from Kleihauer positive blood) correspond respectively to A, B, C, and D, an analysis in FL1 and FL2 of the populations of events as represented in the scale in FIG. 2 can be observed. FIG. 3B effectively corresponds to the respresentation of FIG. 2 which is similar to representations corresponding to FIG. 3A, C and D.

In the figures, FL1 corresponds to the expression of the foetal haemoglobin and FL2 to the expression of i. The band on the left defined by abscisse=1 contains the events corresponding to adult erythrocytes and a clear distinction between the adult and foetal erythrocytes is noticed. In FIG. 3B, the events which do not exist in FIG. 3A and which correspond to cord blood which has been added to the adult blood are observed in window F. In FIG. 3D, events which do not exist in FIG. 3C and which correspond to foetal erythrocytes which circulated in the blood of a woman after foetal haemorrhage are observed in window F.

It can be concluded from the preceding that the method and detection reagents for foetal red corpuscles of the invention have been proved effective in a model in which cord blood was added to adult blood and equally in the case of foetal haemorrhage of pregnant women.

It can equally be concluded from the preceding that the method and reagents above allow the detection of the gamma chain of haemoglobin in red corpuscles. In addition to the case of foetal haemorrhage in pregnant women, the method can in particular be applied in the case of thalassaemia, sickle cell anemia and iron deficiency in pregnant women, etc. The method and reagents also allow the detection of the foetal or non-foetal origin of a red corpuscle by the presence or absence of the blood group i.

What is claimed is:

1. A kit for permeabilizing erythrocytes comprising
   (a) a liquid isotonic or hypertonic fixing agent at pH 4 to 7 containing an aliphatic $C_1$–$C_5$ aldehyde which is present in a concentration of from 1.5M to 10M and a disaccharide which is present in a concentration of from 0.025M to 1.32M,
   (b) a permeabilizing agent at pH 3 to 8 containing a detergent selected from the group consisting of Zwitterionic and anionic detergents, and an oligosaccharide; and
   (c) two antibodies against fetal antigens which are expressed independently on the fetal erythrocytes.

2. A kit according to claim 1, wherein the two antibodies against two fetal antigens which are expressed independently on the erythrocyte are marked with two different fluorescent markers.

3. A kit according to claim 2, wherein the two fetal antigens which are expressed independently on the erythrocyte are fetal hemoglobin found inside the cell, and antigen i found on the outside of the cell.

4. A kit according to claim 1 wherein the two fetal antigens which are expressed independently on the erythrocyte are fetal hemoglobin found inside the cell, and antigen i found on the outside of the cell.

5. A kit according to claim 1, wherein monoclonal antibody NaM16-2F4 of IgG1 typw deposited at the Collection Nationale de Microorganismes (CNCM) in Paris on Jun. 23, 1998 under No. I-2044 is used for marking the fetal hemoglobin, and monoclonal antibody NaM61-1A2 of IgM type deposited at the Collection Nationale de Microorganismes (CNCM) at Paris on Jun. 23, 1998 under No. I-2043 is used for marking the antigen i.

6. The kit according to claim 1 wherein the detergent is present in an amount to permeabilize the fetal erythrocytes.

7. A kit according to claim 1 wherein the two antibodies against two fetal antigens which are expressed independently on the erythrocyte are marked with two different fluorescent markers;

wherein the monoclonal antibody NaM16-2F4 or IgG1 type deposited at the Collection National de Microorganisms (CNCM) in Paris on Jun. 23, 1998 under No. I-2044 is used for marking the fetal hemoglobin, and monoclonal antibody NaM61-1A2 of IgM type deposited at the Collection National de Microorganisms (CNCM) in Paris on June $23^{rd}$ under No. I-2043 is used for marking the antigen i.

8. The kit according to claim 7, wherein one antibody is an antibody against fetal hemoglobin, which antigen is found inside the cell, and the other antibody is an antibody to an i antigen, which antigen is found outside the cell.

9. The kit according to claim 1 wherein one of the two antibodies against fetal antigens is found inside the cell and the other of the two antibodies against fetal antigens is found inside the cell.

* * * * *